US00PP09246P

United States Patent [19]

Egger

[11] Patent Number: Plant 9,246

[45] Date of Patent: Aug. 15, 1995

[54] *LONGIFLORUM*×ASIATIC HYBRID LILY PLANT NAMED 'CEB DREAM'

[75] Inventor: Donald L. Egger, Aurora, Oreg.

[73] Assignee: Cebeco Lilies, Inc., Aurora, Oreg.

[21] Appl. No.: 333,492

[22] Filed: Nov. 2, 1994

[51] Int. Cl.[6] ..... A01H 5/00
[52] U.S. Cl. ..... Plt./87.4
[58] Field of Search ..... Plt. 87.4

*Primary Examiner*—James R. Feyrer
*Attorney, Agent, or Firm*—Klarquist Sparkman Campbell Leigh & Whinston

[57] ABSTRACT

A new and distinct lily hybrid named 'Ceb Dream' characterized by numerous upright, large, unspotted, soft pink flowers with contrasting brown anthers on tall, strong stems excellent for cut flower production.

1 Drawing Sheet

BACKGROUND OF THE INVENTION

The present invention comprises a new and distinct cultivar of lily hybrid, referred to commercially as a *longiflorum*-Asiatic Lily Hybrid, referred to by the cultivar name 'Ceb Dream'.

This invention is the product of a controlled breeding program in Aurora, Oreg. The seed parent was a proprietary non-released unnamed Ace×Gold Nugget seedling. The pollen parent was PAM #2, another proprietary non-released plant.

The *longiflorum*-Asiatic cross is relatively new to the trade. This type of cross was originally made to create colored *Lilium longiflorum* hybrids. Instead, due to the difficulty in crossing back to *L. longiflorum,* the plants that were developed had to be crossed with Asiatic lilies. As such, the results look more like Asiatic lilies. The resulting hybrids often have several advantages, not necessarily in combination, over an Asiatic lily: (1) often larger flowers; (2) often larger, waxier leaves; (3) hybrid vigor; (4) lower susceptibility to scorch; (5) excellent flower texture and substance; (6) more virus resistance; (7) new and clearer colors; and (8) stronger, sturdier stems.

This invention has not been observed under all possible environmental conditions. The phenotype may vary significantly with variations in environment such as temperature, light intensity, and day length, without, however, any variation in genotype. The following traits have been repeatedly observed in asexually propagated progeny and are determined to be the basic characteristics of this invention which in combination distinguish this lily as a new and distinct cultivar: (1) large, upright flowers of a soft pink color and no spots; (2) high bud count; (3) lovely, light yellow buds; (4) contrasting dark brown anthers; (5) excellent vase life; (6) early bloom time; and (7) uniform, vigorous stems. Bulbs of this plant may be precooled and forced out of season for very uniform cut flower production.

To the inventor's knowledge, there are no other *longiflorum*-Asiatic lily hybrids with this color flower suitable for cut flower forcing on the market.

Asexual reproduction of this new variety has been initially and subsequently accomplished at Cebeco Lilies, Inc. in Aurora, Oreg., by scaling and tissue culture. The resulting plants have shown that the above-mentioned unique features are stable and reproduce true to type in each successive propagation.

Figure 2:
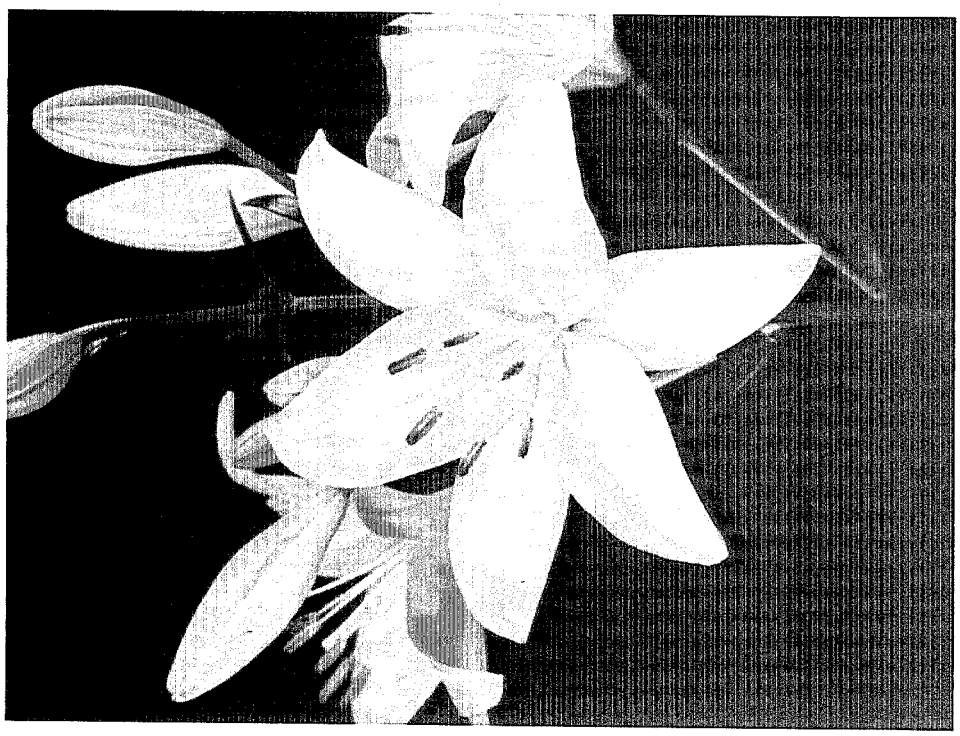
FIG. 2 is a close-up photograph which illustrates in greater detail a single flower of the new plant.
Figure 1:
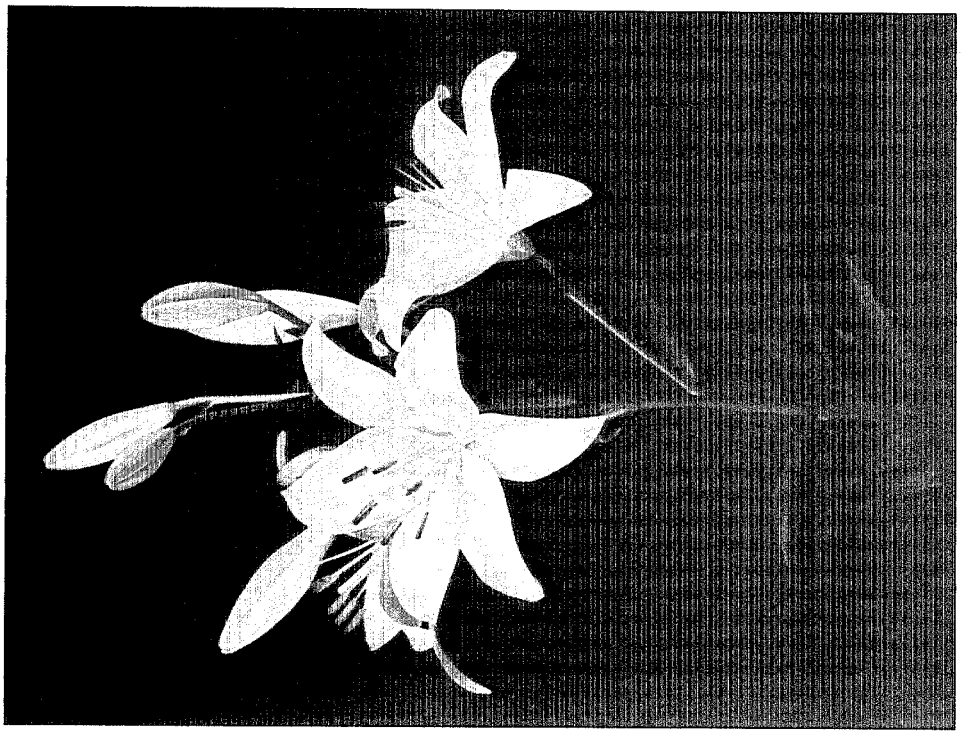
FIG. 1 is a photograph showing the 'Ceb Dream' lily.

The photographs of the drawing were taken in August 1993 in a studio and illustrate the typical flower and foliage form, with color being as true as is reasonably possible in this type of color photograph.

DETAILED DESCRIPTION

The following is a detailed description of the invention based on plants produced under commerical practices in the Cebeco Lilies, Inc. greenhouses in Aurora, Oreg. in July 1993. Color references are made to the Royal Horticultural Society Colour Chart (RHS), except where the context indicates a term having its ordinary dictionary meaning.

THE PLANT

Origin: Seedling.

Parentage:

*Seed parent.*—An unnamed Ace×Gold Nugget seedling.

*Pollen parent.*—PAM #2.

Commercial classification: Upright *longiflorum*-Asiatic hybrid, cut flower type.

Classification: Division VIII, according to the Horticultural Classification of Lilies by the Royal Horticultural Society of London.

Form: Single erect stem bearing terminal cluster of flowers.

Height: About 62 cm. from the top of the soil to the top of the flowers from bulbs of 12 cm. in circumference.

Growth habit: Vigorous, upright and rigid.

Foliage:

*Arrangement.*—Spiral.

*Quantity.*—Average-open.

*Leaf size.*—Variable to about 11 cm. long and about 12 mm. wide.

*Leaf shape.*—Linear to linear-lanceolate with entire margins.

*Texture.*—Leathery.

*Aspect.*—Matte.

*Color.*—Medium green on both sides, closest to 147A.

Bulbs:

*Size.*—Variable, ranging to about 12–14 cm. in circumference as used commercially.

*Color.*—White.

THE BUD

Size: Large, to about 6.5 cm. long and 22 mm. wide just prior to opening.

Shape: Ovoid with an obtuse tip.

Rate of opening: The mature bud opens slowly in response to light.

Color: Creamy yellow. Yellow Group 10D.

THE FLOWER

Blooming habit: Annually, once and early season.

Days to bloom: Flowers approximately 78 days after spring greenhouse planting under typical commercial flower forcing conditions of 15° Celsius night time temperatures.

Inflorescence size: About 18 cm. high and 26 cm. wide when there are five flowers present.

Flower size: Large.

*Diameter.*—About 16 cm.

*Depth.*—About 6 cm.

Borne: In an umbel or modified raceme of 5 to 10 flowers from bulbs 12–14 cm. in circumference.

Shape: When the flower first opens it is bowl-shaped. Later, the shape flattens out and the tepals reflex slightly at the tips.

Tepalage:

*Number.*—Six.

*Arrangement.*—Imbricated.

*Shape.*—Ovate.

*Texture.*—Spongy, waxy.

*Aspect.*—Matte.

*Size.*—Length: About 10.5 cm. Width: Inner tepals — about 40 mm. Outer tepals — about 31 mm. Depth of imbrication: About 11 mm.

*Nectary.*—About 1 cm. long; yellow green; lightly pubescent; with the channels close together.

*Projections.*—None.

*Spots.*—None.

*Blush.*—Very slight, immediately above the nectary and up the main vein, darker pink, Red Group 37B.

*Color.*—Topside: Soft Light Pink. Young newly open tepal edges are creamy yellow, Yellow Group 11C-D. Mature tepals blend from soft orange pink edges, Orange Group 27C to pink centers, Red Group 36C. Bottomside: Light Pink. Closest to Red Group 36B.

*Discoloration.*—Lightens with age.

*Fragrance.*—slight.

*Lasting quality.*—Excellent.

Pedicel:

*Length.*—Long, usually about 11 cm. (varies from 3–15 cm.).

*Color.*—Yellow-green.

*Orientation.*—Ascending upwardly from about 40°–60° from the horizontal.

THE REPRODUCTIVE ORGANS

Stamens:

*Number.*—Six, typical of the genus Lilium.

*Anthers before dehiscence.*—Size: About 1.6 cm. Color: Two-toned, with brown on top, Grayed-Orange Group 175C and orange on the bottom, Grayed-Orange Group 167C.

*Filaments.*—Length: About 7 cm.

Color: White. White Group 155D.

*Pollen.*—Color: Two-toned. Brown and orange. Grayed-Orange Group 167A.

Pistil:

*Number.*—One.

*Style.*—Length: About 5 cm. Color: Seeming Light Pink overall. Actual color light yellow-orange, Yellow-Orange Group 18C near stigma to light pink, Red Group 27D in the middle to near white, Yellow Group 11D at base.

*Stigma.*—Color: Light Yellow, Yellow Group 9D.

THE FRUIT

Fertility: The fruit is of low fertility.

Shape: Ovoid.

Color at maturity: Soft Brown.

I claim:

1. A new and distinct cultivar of *longiflorum*-Asiatic hybrid lily plant substantially as herein shown and described.

* * * * *